US011160481B2

(12) United States Patent
Zeidan et al.

(10) Patent No.: US 11,160,481 B2
(45) Date of Patent: Nov. 2, 2021

(54) ATRIAL FIBRILLATION MAPPING USING ATRIAL FIBRILLATION CYCLE LENGTH (AFCL) GRADIENTS

(71) Applicants: Biosense Webster (Israel) Ltd., Yokneam (IL); Carlo Pappone, Cernusco Lombardone (IT)

(72) Inventors: Ziyad Zeidan, Zemmer (IL); Aharon Turgeman, Zichron Ya'acov (IL); Benjamin Cohen, Haifa (IL); Meir Bar-Tal, Haifa (IL); Tal Haim Bar-on, Kiryat Tivon (IL); Carlo Pappone, Cernusco Lombardone (IT)

(73) Assignee: Biosense Webster (Israel) Ltd., Yokneam (IL)

(*) Notice: Subject to any disclaimer, the term of this patent is extended or adjusted under 35 U.S.C. 154(b) by 192 days.

(21) Appl. No.: 16/108,863

(22) Filed: Aug. 22, 2018

(65) Prior Publication Data

US 2020/0060567 A1 Feb. 27, 2020

(51) Int. Cl.
*A61B 5/287* (2021.01)
*A61B 18/14* (2006.01)
(Continued)

(52) U.S. Cl.
CPC .............. *A61B 5/287* (2021.01); *A61B 5/361* (2021.01); *A61B 18/1492* (2013.01); *A61B 5/316* (2021.01); *A61B 5/6852* (2013.01); *A61B 2018/00351* (2013.01); *A61B 2018/00577* (2013.01); *A61B 2018/00791* (2013.01); *A61B 2018/00839* (2013.01)

(58) Field of Classification Search
CPC ...... A61B 18/1492; A61B 2018/00839; A61B 2018/00791; A61B 2018/00577; A61B 2018/00351; A61B 5/6852; A61B 5/04012; A61B 5/6858; A61B 5/287; A61B 5/361; A61B 5/742; A61B 5/316; A61N 5/7239
See application file for complete search history.

(56) References Cited

U.S. PATENT DOCUMENTS

2003/0023130 A1   1/2003   Ciaccio et al.
2005/0288599 A1*  12/2005  MacAdam ......... A61B 5/04014
                                                      600/509
(Continued)

FOREIGN PATENT DOCUMENTS

WO    WO2015120064 A1    8/2015
WO    WO 2017/024107 A1  2/2017

OTHER PUBLICATIONS

Pending U.S. Appl. No. 15/986,238, filed May 22, 2018.
(Continued)

*Primary Examiner* — Gary Jackson
*Assistant Examiner* — Sebastian X Lukjan

(57) ABSTRACT

A method including calculating, at multiple intra-cardiac locations, respective average atrial fibrillation cycle-length (AFCL) values. A determination is made as to whether the calculated average AFCL values are indicative of a regular atrial fibrillation (AF) activity. Gradients between pairs of the average AFCL values are calculated for a plurality of average AFCL values that are determined to be indicative of regular AF activity. The calculated AFCL gradients are presented to a user, overlaid on a map of at least a portion of the heart.

18 Claims, 3 Drawing Sheets

(51) Int. Cl.
*A61B 5/361* (2021.01)
*A61B 5/00* (2006.01)
*A61B 18/00* (2006.01)
*A61B 5/316* (2021.01)

(56) References Cited

U.S. PATENT DOCUMENTS

| | | | |
|---|---|---|---|
| 2012/0078129 A1* | 3/2012 | Bailin | A61B 5/042 600/508 |
| 2016/0106376 A1* | 4/2016 | Li | A61B 5/0538 600/373 |
| 2017/0202515 A1 | 7/2017 | Zrihem et al. | |
| 2017/0224239 A1* | 8/2017 | Ng | A61B 5/046 |
| 2018/0042504 A1 | 2/2018 | Botzer et al. | |

OTHER PUBLICATIONS

European Search Report for corresponding EPA No. 19192897.7 dated Jan. 24, 2020.
Seungyup Lee, et al., "An Algorithm to Measure Beat-to-Bet Cycle Lengths for Assessment of Atrial Electrogram Rate and Regularity During Atrial Fibrillation", Journal of Cardiovascular Electrophysiology, vol. 24, No. 2, pp. 199-206, Feb. 9, 2013.
Sajiv M. Narayan et al., "Evaluating Fluctuations in Human Atrial Fibrillatory Cycle Length Using Monophasic Action Potentials", Pace—Pacing and Clinical Electrophysiology, vol. 29, No. 11, pp. 1209-1218, Nov. 1, 2006.

\* cited by examiner

ATRIAL FIBRILLATION MAPPING USING ATRIAL FIBRILLATION CYCLE LENGTH (AFCL) GRADIENTS

FIELD OF THE INVENTION

The present invention relates generally to intrabody electrophysiological mapping using probes, and particularly to cardiac electro-anatomical mapping.

BACKGROUND OF THE INVENTION

Invasive cardiac procedures often employ techniques for mapping electro-anatomical properties of cardiac tissue. For example, U.S. Patent Application Publication 2005/0288599 describes systems and methods to assist in locating the focus of an atrial fibrillation. The systems and methods include the association of atrial fibrillation cycle length values and statistics relating thereto with temporal locations on an electrogram of a given electrode, and/or the coordination of electrode locations with respective the spectral analyses of electrogram signals and further parameters and statistics relating thereto. Ablation therapy can proceed under guidance of such information.

As another example, International Patent Application Publication PCT/US2016/045483 describes cardiac mapping catheters and methods for using the catheters. The catheter can detect the presence, direction and/or source of a depolarization wave front associated with cardiac arrhythmia. A mapping catheter includes a plurality of bipolar electrode pairs in which the members of each pair are opposed to one another across a perimeter, for instance in a circular pattern. The spaced arrangement of the electrodes can be utilized to identify directional paths of moving electric fields or wave fronts in any direction passing across the endocardial surface. The catheters can be used to identify locations and types of triggers and/or drivers of cardiac arrhythmia including rotors, ectopic trigger foci and/or to delineate reentrant pathways.

U.S. Patent Application Publication 2003/0023130 describes a method for identifying and localizing a reentrant circuit isthmus in a heart of a subject during sinus rhythm, including: a) receiving electrogram signals from the heart during sinus rhythm via electrodes; b) storing the electrogram signals; c) creating a map based on the electrogram signals; d) finding a center reference activation location on the map; e) defining measurement vectors originating from the center reference activation location; f) selecting from the measurement vectors a primary axis vector indicating a location of the reentrant circuit isthmus in the heart; g) finding threshold points of electrogram signals on the map; h) connecting the threshold points to form a polygon indicating a shape of the reentrant circuit isthmus in the heart.

U.S. Patent Application Publication 2017/0202515 describes a method of atrial rotational activity pattern (RAP) source detection that includes detecting, via a plurality of sensors, electro-cardiogram (ECG) signals over time, each ECG signal detected via one of the plurality of sensors and indicating electrical activity of a heart. The method also includes determining, for each of the plurality of ECG signals, one or more local activation times (LATs) each indicating a time of activation of a corresponding ECG signal. The method further includes detecting whether one or more RAP source areas of activation in the heart is indicated based on the detected ECG signals and the one or more local LATs. Mapping information of the detected RAP source areas of activation in the heart is also generated for providing one or more maps.

SUMMARY OF THE INVENTION

An embodiment of the present invention provides a method including calculating, at multiple intra-cardiac locations, respective average atrial fibrillation cycle-length (AFCL) values. A determination is made as to whether the calculated average AFCL values are indicative of a regular atrial fibrillation (AF) activity. Gradients between pairs of the average AFCL values are calculated for a plurality of average AFCL values that are determined to be indicative of regular AF activity. The calculated AFCL gradients are presented to a user, overlaid on a map of at least a portion of the heart.

In some embodiments, the method includes checking whether the average AFCL value is between a preset lower limit and a preset upper limit. In some embodiments, the method includes checking whether a standard deviation (SD) of the average AFCL value is smaller than a preset SD limit.

In an embodiment, the method includes calculating an AFCL gradient for a pair of average AFCL values that were derived from electrocardiograms acquired at different times. In another embodiment, the method includes color-coding the AFCL gradients according to at least sizes and directions of the AFCL gradients.

In some embodiments, the method includes denoting on the map arrows indicative of locations at which the AF originates, or through which the AF propagates. In some embodiments, the method includes displaying on the map an animation comprising at least one of initiation and propagation of the regular AF activity.

In an embodiment, the method further includes comprising presenting the average AFCL values to the user, overlaid on the map. In another embodiment, the method includes color-coding locations on the map according to the average AFCL values at the locations.

There is additionally provided, in accordance with an embodiment of the present invention, a system including a memory and a processor. The memory is configured to store atrial fibrillation cycle-length (AFCL) values corresponding to respective multiple intra-cardiac locations. The processor is configured to calculate from the stored AFCL values, average AFCL values at the respective multiple intra-cardiac locations, and to determine whether the calculated average AFCL values are indicative of a regular atrial fibrillation (AF) activity. The processor is further configured to, for a plurality of average AFCL values that are determined to be indicative of regular AF activity, calculate gradients between pairs of the average AFCL values, and to present the calculated AFCL gradients to a user, overlaid on a map of at least a portion of the heart.

The present invention will be more fully understood from the following detailed description of the embodiments thereof, taken together with the drawings in which:

DETAILED DESCRIPTION OF EMBODIMENTS

Overview

Figure 1:
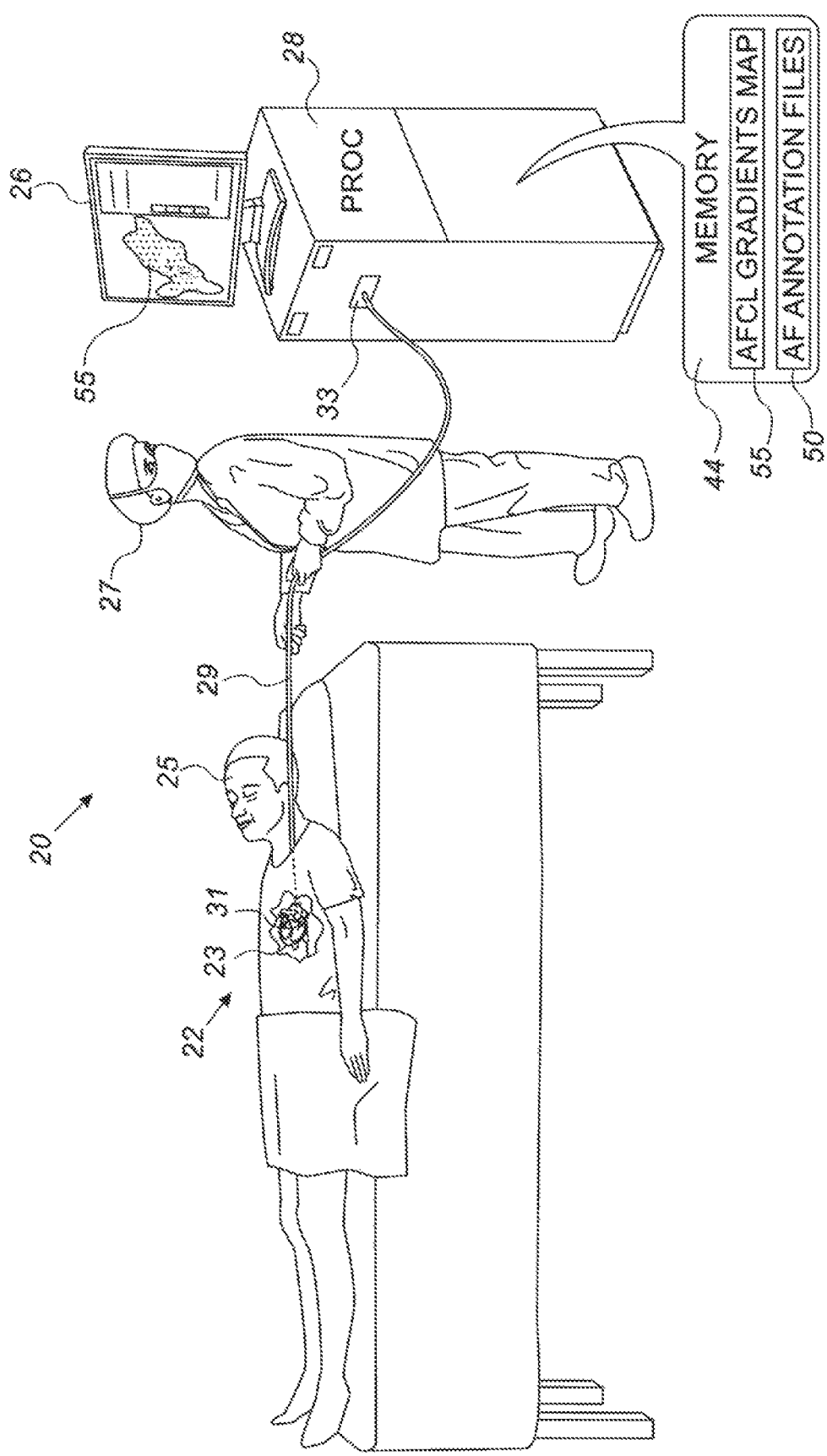
FIG. 1 is a schematic, pictorial illustration of a cardiac electro-anatomical mapping system, in accordance with an embodiment of the present invention.

Embodiments of the present invention that are described hereinafter provide improved methods and systems for the electrophysiological (EP) characterization, and electro-anatomical mapping, of atrial fibrillation (AF). The disclosed techniques are applicable to the characterization and mapping of various types of aberrant cardiac EP activity, such as paroxysmal AF, persistent AF, or long-standing AF.

The disclosed techniques utilize an empirical observation that the AFCL is variable among various anatomical locations, and over time at a same location as well. Nevertheless, AFCL is regular at locations of AF activation origins (drivers) and becomes less regular as activation propagates away from those locations. In the present context, a regular pattern of arrhythmia is characterized as having a regular, i.e., relatively unchanging, as defined below, AF cycle-length (AFCL) value. An AFCL value (not necessarily a regular one) refers to a time interval between two electrical activation events at a certain intra-cardiac location (e.g., on a surface of a cavity of the heart).

An example catheter-based system and technique for automatically identifying activations and calculating AFCL values from intra-cardiac electrograms that exhibit AF or other arrhythmic behavior at a respective intra-cardiac location is described in U.S. patent application Ser. No. 15/986,238, entitled "Identifying Activations in an Atrial Fibrillation Electrogram," filed May 22, 2018, whose disclosure is incorporated herein by reference.

In some embodiments described herein, a processor first determines whether a characteristic regular AFCL value exists at each of multiple intra-cardiac locations that are electro-anatomically mapped. In some embodiments, the processor determines the existence of a regular AFCL value at a given intra-cardiac location based on performing statistical analysis over a set of AFCL values, which, for example, the processor calculates at the location using the method described in U.S. patent application Ser. No. 15/986,238, cited above. Another method for identifying AF activations, which is based on unipolar electrocardiogram signals, is described in U.S. Patent application publication 2018/0042504, entitled "Annotation of a Wavefront," filed Feb. 15, 2018, whose disclosure is incorporated herein by reference. In an embodiment, the processor determines, for each distribution (i.e., set) of AFCL values (a) whether the average AFCL value lies between a preset lower limit and a preset upper limit, and (b) whether a standard deviation (SD) of the average AFCL value is smaller than a preset SD limit.

In some embodiments of the present invention, a processor retrieves sets of AFCL values by uploading "AFCL files," each file containing a set of calculated AFCL values for every given intra-cardiac location. Next, as described above, the processor calculates, for each set, the average AFCL value and its SD, so as to determine whether a regular pattern of arrythmia exists at each of the locations. In an embodiment, the processor displays, to a user, the determined regular average AFCL values, overlaid on an anatomical map of at least a portion of a heart of a patient.

The disclosed embodiments further utilize another empirical observation, that gradients of regular AF patterns are well correlated with, and thus indicative of, useful clinical information, e.g., the directions of AF wave fronts propagation, the locations of activation origins (drivers, sources) over tissue of AF activation, as well as the regular patterns of the AF activation. In other words, the regular AFCL gradient is indicative and predicts AF wavelets and activation patterns in the heart chamber. For example, a positive regular AFCL gradient between a location at one of the pulmonary veins and a location at the left atrium may indicate an AF originating from the pulmonary vein and propagating into the left atrium. In such a case, the regular AFCL gradient map may indicate which pulmonary vein to isolate.

In an embodiment, the processor calculates regular AFCL gradients (i.e., the sizes and directions of differences between AFCL averages of neighboring locations over cardiac tissue). Next, the processor generates an electro-anatomical map depicting the AFCL gradients overlaid on at least a portion of the heart. Finally, the processor presents to a user the gradient map (i.e., gradients, size, and direction that are overlaid on an anatomical map of at least a portion of a heart of a patient).

In some embodiments, the processor emphasizes the AFCL averages and gradients on the map using one or more graphical schemes, such as color coding of intra-cardiac locations according to respective gradient values and/or directions, and/or average AFCL values at the locations. In an embodiment, the processor displays an animation of an initiation and/or propagation of a regular AF activity, by showing, for example, dynamic (i.e., transient) color coding of regular AFCL values overlaid on a map of at least a portion of the heart. In some embodiments, the processor provides the gradient information in the form of vectors, which are overlaid on the map.

The disclosed AFCL gradient map is highly useful as a tool in assisting diagnosis of AF. In contrast to other AF mapping schemes which necessitate simultaneous recording of electrical signals from multiple locations of atria, e.g., mapping based on Local Activation Times (LAT) or phase analysis, the AFCL gradient map is much easier to obtain. Other AF mapping schemes have a significant limitation of collecting electrical data simultaneously from the entire heart chamber, as there is no, so far, a sufficient catheter enabling that precisely. Moreover, applying the approach of regional simultaneous mapping faces the inability to stich the mapped regions to produce a single, consistent, map, because there is no consistent reference that could be used in AF, in contrast to regular arrhythmias such as Atrial Flutter or Atrial Tachycardia.

An AFCL gradient map, on the other hand, may be derived computationally from a set of electrocardiograms collected by a single regular mapping catheter; e.g., a linear or multi electrode catheter. The collected electrical data at each location is analyzed independently of other locations and later all these locations are combined according to AFCL regularity. Using this approach, the disclosed regular AFCL Gradient method enables combining (stitching) AF electrical data at various anatomical locations which were not collected simultaneously. In an embodiment, an AFCL gradient is calculated that way using for a pair of average AFCL values that were derived from electrocardiograms acquired at different times.

Thus, the disclosed AFCL gradient mapping technique may simplify the mapping of AF by minimizing invasive probing required during the diagnostic procedure, eliminating the need for simultaneous recording and overcoming its limitations.

System Description

FIG. 1 is a schematic, pictorial illustration of a cardiac electro-anatomical mapping system 20, in accordance with an embodiment of the present invention. In some embodiments, system 20 is configured to acquire intra-cardiac electrograms from multiple intra-cardiac locations (of a heart 23 of a patient 25) and to analyze the electrograms to determine which of the locations demonstrate a regular CL of AF, as described above. For example, system 20 is configured to calculate, analyze, and display a map 55 of regular AFCL averages and/or gradients of the regular AFCL averages, so as to indicate locations of potential origin of the arrhythmia over cardiac tissue for potential treatment of the arrhythmia, such as by ablation.

System 20 typically acquires the electrograms using a catheter 29, such as the Lasso® or Pentaray® catheters (both produced by Biosense-Webster, Irvine, Calif.), which comprise multiple distal-electrodes 22 fitted at a distal-end 31. The acquired electrograms can be derived from bipolar signals and/or from unipolar signals. In bipolar acquisition, the signal represents the voltage between a respective pair of distal-electrodes 22. In unipolar acquisition, the signal represents the voltage between one of distal-electrodes 22 and a reference electrode that is coupled externally to patient 25.

The signals are transmitted to a processor 28 via an electrical interface 33 to which a proximal end of catheter 29 is connected. Processor 28 calculates from the electrograms, at each intra-cardiac location, a respective set of AFCL values, based on activation annotations of bipolar or unipolar signals. In some embodiments, processor 28 stores the different sets of the calculated AFCL values in AF annotation files 50 in a memory 44, wherein each AF annotation file 50 contains a set of AFCL values derived from a distinct intra-cardiac location, to be further analyzed to determine if regular AF activity occurs at each location.

As noted above, a catheter-based system and technique that automatically identify AF activations and enables calculating AFCL values from intra-cardiac electrograms exhibiting atrial fibrillation or other arrhythmic behavior is provided by U.S. patent application Ser. No. 15/986,238, cited above.

In some embodiments, processor 28 calculates, from each of the sets of AFCL values in AF annotation files 50, an average AFCL and a standard-deviation (SD) of the average AFCL at the intra-cardiac location. If the average AFCL value at the location falls between preset lower and upper limits, such as 100 mSec<average AFCL<300 mSec, and if its SD is smaller than a preset SD value, such as SD<30 mSec, the processor categorizes the intra-cardiac location as a location where a regular pattern of AF occurs. The processor further assigns to that location the calculated average AFCL value, for example, for presentation in an electro-anatomical map. In an embodiment, for improving the analysis, the system may ignore extreme values of AFCL, as below 10 percentile and above 90 percentiles.

In some embodiments, for example, in long recording sections of 20-30 sec, regular patterns may appear for several seconds and in different events throughout the recorded section, with variability in SD among these events. In this case the determination of regularity, average AFCL and SD for each event could be made by processor 28 calculating these parameters in a moving time window of 2-3 sec, for example. Then processor 28 selects only the most regular time segment (e.g., based on minimal SD), and drops the remaining segments, even if the AFCL parameters of one or more of the other segments are within the limits.

In some embodiments, processor 28 calculates AFCL gradients in order to generate AFCL gradient map 55 of at least part of the intra-cardiac tissue of heart 23 of patient 25. In an embodiment, processor 28 overlays, at respective locations on map 55, the calculated gradients (e.g., in form of vectors) to indicate where an AF may originate or through which it may propagate. In another embodiment, the processor stores AFCL gradient map 55 in memory 44.

Processor 28 is further configured to present AFCL gradient map 55 on a display 26. For example, the processor displays a completed portion of AFCL gradient map 55 while the rest of the map is still being calculated.

In general, processor 28 may be embodied as a single processor, or as a cooperatively networked or clustered set of processors running software enabling the processor to perform the tasks described herein. The software may be downloaded to processor 28 in electronic form, over a network, for example, or it may, alternatively or additionally, be provided and/or stored on non-transitory tangible media, such as magnetic, optical, or electronic memory.

Atrial Fibrillation Mapping Using Cycle-Length Gradients

Figure 2:
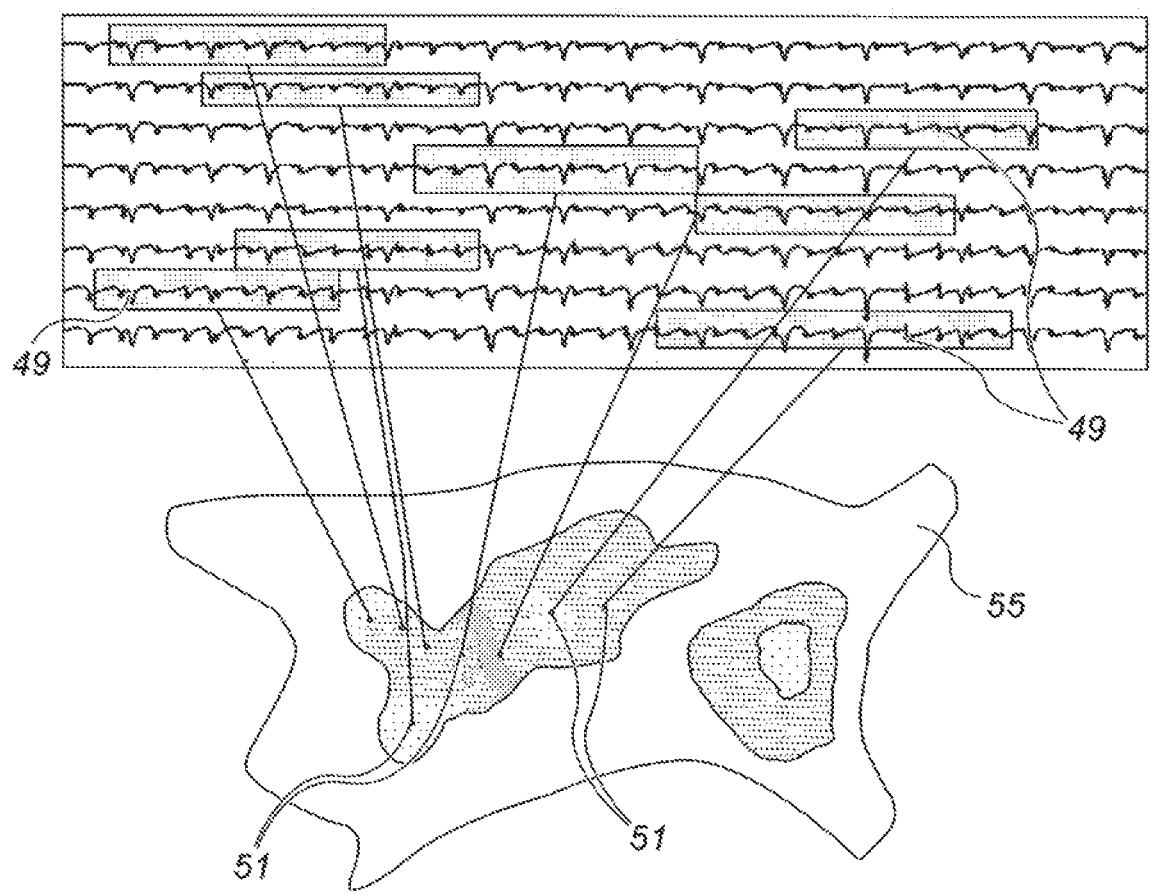
FIG. 2 is a schematic, pictorial illustration of an electro-anatomical map of cardiac tissue overlaid with intra-cardiac locations that demonstrate regular AF activity, in accordance with an embodiment of the present invention.

FIG. 2 is a schematic, pictorial illustration of an electro-anatomical map of cardiac tissue overlaid with intra-cardiac locations that demonstrate regular AF activity, in accordance with an embodiment of the present invention. In some embodiments, as noted above, the processor indicates a location 51 as a location of regular AF activity, based on analyzing a respective annotated ECG time-segment 49 (i.e., that was recorded at the location). In an embodiment, processor 28 determines, based on respective annotated ECG time-segment 49, that the average and SD of the AFCL value calculated for time-segment 49 are within the limits given above.

Processor 28 then overlays each of locations 51 and the respectively calculated average AFCL value at each location 51 on map 55 for further processing into a gradient map, as described below.

Figure 3A:
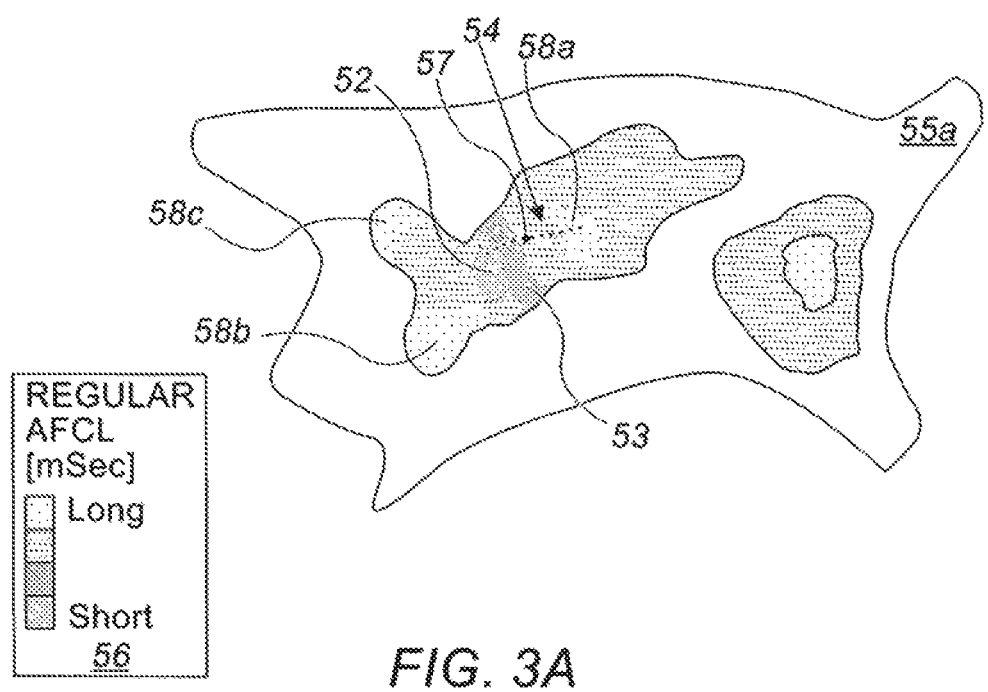
FIGS. 3A and 3B are schematic, pictorial illustrations of AFCL gradient maps of a portion of cardiac tissue, in accordance with embodiments of the present invention.
Figure 3B:
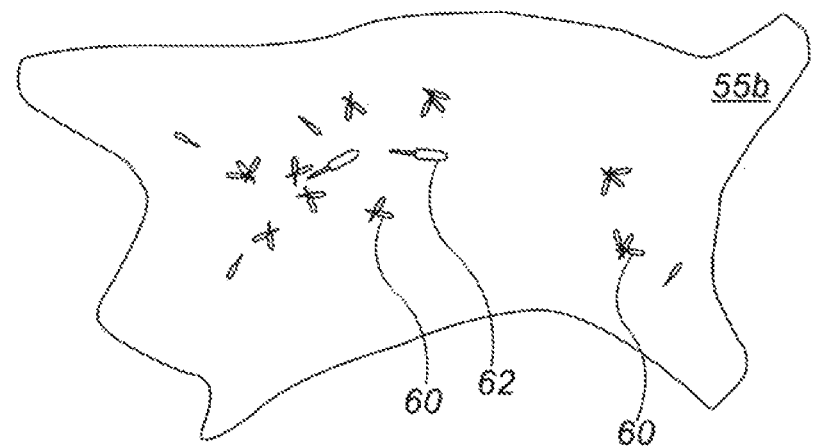

FIGS. 3A and 3B are a schematic, pictorial illustration of an AFCL gradient maps 55a and 55b, respectively, of a portion of cardiac tissue, in accordance with embodiments of the present invention. Maps 55a and 55b may be presented to a user on display 26 of mapping system 20.

The horizontal and vertical directions of maps 55a and 55b denote spatial location over cardiac tissue. In the example brought by FIGS. 3A and 3B, maps 55a and 55b are of the left atrium of heart 23.

FIG. 3A shows an isochronal map 55a, in which the displayed gray levels describe a varying value of the local average AFCL, are overlaid on an anatomical map, to indicate a local direction and size of the AFCL gradients. A legend 56 provides gray-level coding of the displayed average AFCL values. In an embodiment 100 mSec represents "Short" and 250 mSec represents "Long." Contours 53 indicate the iso-value AFCL (e.g., by means of presentation of a topographic map).

As seen in FIG. 3A, an "inner," darkly shaded, region has a shortest average AFCL. Lightly shaded, "Perimetrical" regions 58A, 58B and 58C have longest average AFCL values. In between, there are regions with intermediate shades and, correspondingly, intermediate average AFCL values. The changing shades are thus indicative of the size and direction of the AFCL gradients.

Multiple activation points around region 52, as FIGS. 3A and 3B indicate, with activation propagating from region 52 "outwards" to perimeter locations (as seen in the vector map FIG. 3B) indicates that a regular AF activation is originating at region 52.

By way of example, the positive difference in regular in AFCL value between region 58 and region 52, combined with other indications, such as the anatomical nature of the locations, the width and number of shaded regions, and the value of the short AFCL (i.e., at region 52), indicates that activation propagates from location 52 towards location 58A. Combined with other indications, such as the anatomical nature of the locations, and, for example, the value of the AFCL at region 52, may indicate that location 52 is a potential source of AF. Based on the indication, physician 27 may consider this location as a potential source of AF and potential target for ablation Path 54 indicates a likely propagation route and direction of any AF activity originating at location 52. In an embodiment, location 52 is in a pulmonary vein, location 58 is at the left atrium, and location 57 is at the ostium of the pulmonary vein. By way of example, a location 57 on path 54 may be a candidate location for an ablation, so as to cut off AF propagation from location 52 to location 58A.

FIG. 3B is a vector map 55b, which displays minor gradient vectors 60 and major gradient vectors 62, overlaid on anatomical map 55. The darker and thicker part of the vectors are aligned at a direction of the vector point at. In an embodiment, minor gradient vectors 60 are calculated from a set of regular AFCL locations 51 on map 55 having regular AFCL values (shown in FIG. 2). Each minor gradient vector 60 is an average of two differences over a triangle defined by three-neighboring locations (not shown) of the set of locations 51. A major gradient vector 62 is an average of two or more minor gradient vectors. As seen, both the isochronal map and the vector map indicate of a similar path through which an AF propagates over tissue of the depicted left atrium anatomy.

The example illustration shown in FIGS. 3A and 3B are chosen purely for the sake of simplicity and conceptual clarity. Visual elements that emphasize potential locations and paths of AF activation may be included, as well as numbers, such as a regular AFCL value displayed at each location. In an embodiment, an animated AFCL Gradient propagation map (not shown), dynamically demonstrates the changes of AFCL over the anatomy, for example on display 26.

In some embodiments, FIG. 3B is presented overlaid on FIG. 3A, e.g., having vectors 60 are overlaid on the greylevel shading to indicate a local direction and size of the AFCL gradients.

Figure 4:
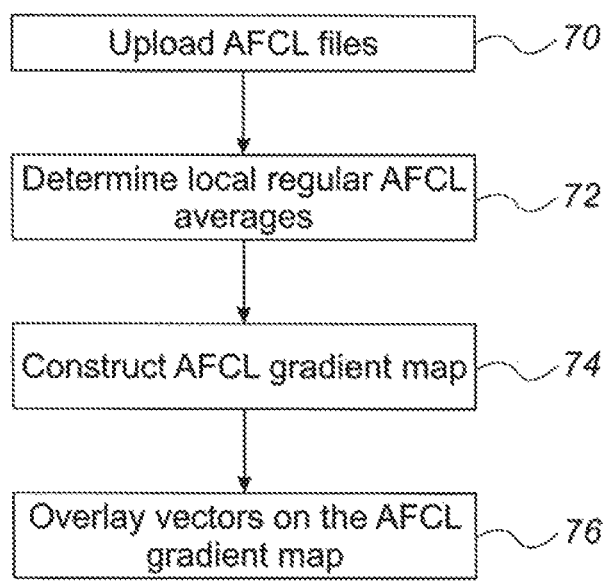
FIG. 4 is a flow chart that schematically illustrates a method for generating and using an AFCL gradient map, in accordance with an embodiment of the present invention.

FIG. 4 is a flow chart that schematically illustrates a method for generating and using an AFCL gradient map 55b, in accordance with an embodiment of the present invention. The process of generating AFCL gradient map 55b begins by processor 28 uploading sets of AFCL values of corresponding locations over cardiac tissue, at an AFCL files uploading step 70.

Processor 28 applies statistical analysis to each of the AFCL sets, so as to determine regular patterns of AF, at an AFCL analysis step 72. Next, processor 28 calculates AFCL gradients between pairs of average AFCL values of adjacent locations 51, and constructs AFCL gradient map 55b, at an AFCL gradient mapping step 74. Finally, processor 28 overlays on map 55b AF arrows comprising size and direction (i.e., vectors) of AFCL gradients, at an arrow overlaying step 76. The arrows are indicative of locations at which the AF originates, or through which the AF propagates. The process may continue to display map 55b with the additional indications of an aberrant cardiac activity at cardiac locations, on display 48.

The example flow chart shown in FIG. 3 is chosen purely for the sake of conceptual clarity. In alternative embodiments, for example, processor 28 generates an animation of the AFCL values of successive propagating electrical activation events. Although the embodiments described herein mainly address specific cardiac applications, the methods and systems described herein can also be used in other cardiac applications.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method for atrial fibrillation mapping using atrial fibrillation cycle length gradients, the method comprising:
    calculating, at multiple intra-cardiac locations, respective average atrial fibrillation cycle-length (AFCL) values, wherein the multiple intra-cardiac locations are different locations relative to a source of atrial fibrillation;
    determining, utilizing statistical analysis, whether the calculated average AFCL values are indicative of a regular atrial fibrillation (AF) activity for all of the multiple intra-cardiac locations;
    for a plurality of average AFCL values that are determined to be indicative of regular AF activity, calculating gradients between pairs of the average AFCL values; and
    presenting the calculated AFCL gradients, over time, to a user, overlaid on a map of at least a portion of the heart.

2. The method according to claim 1, wherein determining whether an average AFCL value is indicative of regular AF activity comprises checking whether the average AFCL value is between a preset lower limit and a preset upper limit.

3. The method according to claim 1, wherein determining whether an average AFCL value is indicative of regular AF activity comprises checking whether a standard deviation (SD) of the average AFCL value is smaller than a preset SD limit.

4. The method according to claim 1, wherein calculating the gradients comprises calculating an AFCL gradient for a pair of average AFCL values that were derived from electrocardiograms acquired at different times.

5. The method according to claim 1, wherein presenting the AFCL gradients comprises color-coding the AFCL gradients according to at least sizes and directions of the AFCL gradients.

6. The method according to claim 1, wherein presenting the AFCL gradients comprises denoting on the map arrows indicative of locations at which the AF originates, or through which the AF propagates.

7. The method according to claim 1, wherein presenting the AFCL gradients comprises displaying on the map an animation comprising at least one of initiation and propagation of the regular AF activity.

8. The method according to claim 1, and comprising presenting the average AFCL values to the user, overlaid on the map.

9. The method according to claim 8, wherein presenting the average AFCL values comprises color-coding locations on the map according to the average AFCL values at the locations.

10. A system for atrial fibrillation mapping using atrial fibrillation cycle length gradients, the system comprising:
a memory, which is configured to store atrial fibrillation cycle-length (AFCL) values corresponding to respective multiple intra-cardiac locations; and a processor, which is configured to:
calculate from the stored AFCL values, average AFCL values at the respective multiple intra-cardiac locations, wherein the multiple intra-cardiac locations are different locations relative to a source of atrial fibrillation;
determine, using statistical analysis, whether the calculated average AFCL values are indicative of a regular atrial fibrillation (AF) activity for all of the multiple intra-cardiac locations;
for a plurality of average AFCL values that are determined to be indicative of regular AF activity, calculate gradients, over time, between pairs of the average AFCL values; and
present the calculated AFCL gradients to a user, overlaid on a map of at least a portion of the heart.

11. The system according to claim 10, wherein the processor is configured to determine whether an average AFCL value is indicative of regular AF activity by checking whether the average AFCL value is between a preset lower limit and a preset upper limit.

12. The system according to claim 10, wherein the processor is configured to determine whether an average AFCL value is indicative of regular AF activity by checking whether a standard deviation (SD) of the average AFCL value is smaller than a preset SD limit.

13. The system according to claim 10, wherein the processor is configured to calculate an AFCL gradient for a pair of average AFCL values that were derived from electrocardiograms acquired at different times.

14. The system according to claim 10, wherein the processor is configured to present the AFCL gradients by color-coding the AFCL gradients according to at least sizes and directions of the AFCL gradients.

15. The method according to claim 10, wherein the processor is configured to present the AFCL gradients by denoting on the map arrows indicative of locations at which the AF originates, or through which the AF propagates.

16. The system according to claim 10, wherein the processor is configured to present the AFCL gradients by displaying on the map an animation comprising at least one of initiation and propagation of the regular AF activity.

17. The system according to claim 10, wherein the processor is further configured to present the average AFCL values to the user, overlaid on the map.

18. The system according to claim 10, wherein the processor is configured to present the average AFCL values by color-coding locations on the map according to the average AFCL values at the locations.

* * * * *